United States Patent
Liu

(10) Patent No.: US 10,239,895 B2
(45) Date of Patent: *Mar. 26, 2019

(54) COMPOUND FOR SPECIFICALLY BINDING TO AMYLOID β-PROTEIN

(71) Applicant: NEUBORON MEDTECH LTD., Nanjing, Jiangsu (CN)

(72) Inventor: Yuan-Hao Liu, Jiangsu (CN)

(73) Assignee: NEUBORON MEDTECH LTD., Nanjing, Jiangsu (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/010,890

(22) Filed: Jun. 18, 2018

(65) Prior Publication Data

US 2018/0298037 A1  Oct. 18, 2018

Related U.S. Application Data

(63) Continuation of application No. PCT/CN2016/111815, filed on Dec. 23, 2016.

(30) Foreign Application Priority Data

Dec. 30, 2015 (CN) .......................... 2015 1 1022559

(51) Int. Cl.
| | |
|---|---|
| *C07F 5/02* | (2006.01) |
| *A61K 51/04* | (2006.01) |
| *G01N 33/68* | (2006.01) |
| *A61K 41/00* | (2006.01) |
| *A61N 5/10* | (2006.01) |

(52) U.S. Cl.
CPC .......... *C07F 5/025* (2013.01); *A61K 41/0095* (2013.01); *A61K 51/04* (2013.01); *A61N 5/10* (2013.01); *C07F 5/02* (2013.01); *G01N 33/68* (2013.01); *A61N 2005/109* (2013.01); *A61N 2005/1098* (2013.01); *C07B 2200/05* (2013.01)

(58) Field of Classification Search
CPC ............................ C07F 5/025; A61K 41/0095
See application file for complete search history.

(56) References Cited

U.S. PATENT DOCUMENTS 9,840,509 B2 * 12/2017 Desai ................. A61K 31/4985

FOREIGN PATENT DOCUMENTS

| CN | 1132504 A | 10/1996 |
|---|---|---|
| CN | 103805167 A | 5/2014 |
| WO | 9509838 A1 | 4/1995 |
| WO | 2014003336 A1 | 1/2014 |
| WO | 2015132799 A2 | 9/2015 |

OTHER PUBLICATIONS

International Search Report of PCT/CN2016/111815, dated Apr. 5, 2017.
Cui, Meng-chao et al., Synthesis and biological evaluation of novel benzothiazole derivatives based on the styrene structure as potential beta-amyloid imaging agents, Progress Report on China Nuclear Science & Technology, 2009, 91-94, vol. 1.
Ma et al., The current clinical application of positron emission tomography (PET), Basic Medical Sciences and Clinics, 1999.

* cited by examiner

*Primary Examiner* — Golam M Shameem
(74) *Attorney, Agent, or Firm* — Locke Lord LLP; Tim Tingkang Xia, Esq.

(57) ABSTRACT

Provided is a compound for specifically binding to amyloid β-protein. The compound has thereon a nuclide with a large thermal neutron capture cross section and the compound is capable of specifically binding to the amyloid β-protein. The property of the compound allows it to be used in conjunction with a neutron capture therapy device to eliminate amyloid β-protein. Similarly, when the compound is labelled with radioactive element $^{11}C$, the compound can also be used in conjunction with PET/CT for determining the part of the brain where amyloid β-protein is deposited, for diagnosing Alzheimer's disease. Also disclosed is a preparation process for the compound. The beneficial effect of the present disclosure is to make the therapy and diagnosis of Alzheimer's disease more targeted by providing the compound for specifically binding to amyloid β-protein.

10 Claims, 4 Drawing Sheets

(1)

(2)

Graph A

Graph B

COMPOUND FOR SPECIFICALLY BINDING TO AMYLOID β-PROTEIN

RELATED APPLICATION INFORMATION

This application is a continuation of International Application No. PCT/CN2016/111815, filed on Dec. 23, 2016, which claims priority to Chinese Patent Application No. 201511022559.5, filed on Dec. 30, 2015, the disclosures of which are hereby incorporated by reference.

FIELD OF THE DISCLOSURE

The present disclosure relates to the field of medical technology, and in particularly to a compound for specifically binding to amyloid β-protein, preparation process and use thereof for the preparation of a medicament.

BACKGROUND OF THE DISCLOSURE

The current research shows that the deposition of amyloid β-protein is closely related to the pathogenesis of Alzheimer's disease (AD). Therefore, the detection of amyloid β-protein and how to eliminate or reduce amyloid β-protein have become the focus of research. To further investigate or elimination amyloid β-protein, there is a need for a compound that specifically binds to amyloid β-protein.

With the development of neutron capture therapy technology, the use of neutron capture therapy to eliminate amyloid β-protein has higher targeting and better therapeutic effect, however, no compound has been found that can combine with the neutron capture therapy with the capable of specifically binding to amyloid β-protein.

SUMMARY

In order to solve the above technical problems, an aspect of the present disclosure provides a compound for specifically binding to amyloid β-protein, and the compound has a structure as shown in formula I:

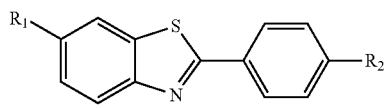

formula I wherein $R_1$ is —$B(OH)_2$, $R_2$ is —$NHCH_3$; and the boron element in $R_1$ is a nuclide $^{10}B$ with a large thermal neutron capture cross section.

The nuclide with a large thermal neutron capture cross section include, but are not limited to, $^{10}B$, $^{155}Gd$ or $^{157}Gd$. Wherein the nuclide with a large thermal neutron capture cross section refers to a nuclide having a neutron capture cross section greater than or equal to 100 times of the neutron capture cross section of the basic constituent elements (C, H, O, N, P, S) of the human body under the same energy of thermal neutron irradiation. Wherein H has the largest neutron capture cross section among the basic constituent elements of the human body under the same energy of thermal neutron irradiation. Under the condition of thermal neutron energy of 0.025 eV, the thermal neutron capture cross section of H is 0.2 barn, the thermal neutron capture cross section of $^{10}B$ is 3800 barn, the thermal neutron capture cross section of $^{155}Gd$ is 60700 barn, and the thermal neutron capture cross section of $^{157}Gd$ is 254000 barn, all are greater than 100 times of the thermal neutron capture cross section of the H element under the same energy of thermal neutron irradiation.

This kind of nuclides with a large thermal neutron capture cross section may react with the thermal neutrons to release at least one lethal radiation that has a short range and substantially destroys the structure of the amyloid β-protein that specifically binds to the compound, without destroying other normal tissue, thus the damage to normal tissue is very little.

The nuclide $^{10}B$ undergoes the following reaction under the irradiation of the neutron beam:

Reaction Formula I

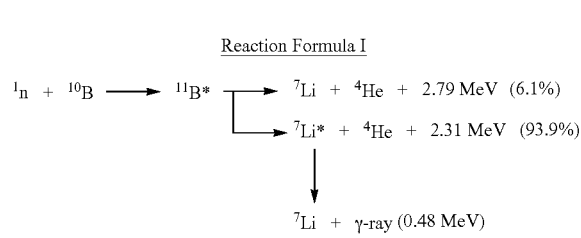

Two heavy particles of $^4He$ and $^7Li$ are generated by $^{10}B(n,\alpha)$ $^7Li$ neutron capture and nuclear splitting reaction utilizing the characteristics of boron-containing ($^{10}B$) compound that with a large thermal neutron capture cross section. As shown in Reaction Formula I, the average energy of the two heavy particles is about 2.33 MeV, with characteristics of high linearity transfer (LET), and short range. The linear energy transfer and range of α particles is 150 keV/nm, 8 nm, respectively, while that of $^7Li$ heavy particles is 175 keV/μm, 5 μm. The total range of the two particles is equivalent to about the size of one cell, so the radiation damage to the organism is limited to the cell level.

The compound has a property of specifically binding to the amyloid β-protein and has a nuclide $^{10}B$ with a large thermal neutron capture cross section. Therefore, after forming a conjugate with the amyloid β-protein, the conjugate is irradiated with a neutron beam generated by a neutron capture therapy device.

It is preferred that in the compound for specifically binding to the amyloid β-protein, the carbon element in $R_2$ of the compound is $^{11}C$.

The element $^{11}C$ as a radionuclide is often used to label compounds for medical diagnosis and use. The compound 2-(4-methylaminophenyl)-6-dihydroxyboroobenzothiazole provided by the present disclosure has a property of specifically binding to the amyloid β-protein, and after labeling the compound with the radionuclide $^{11}C$, the compound can be used in PET/CT to track and determine the parts of amyloid β-protein deposition in the brain for AD diagnosis.

According to another aspect of the present disclosure, there is provided a process for preparing the compound for specifically binding to the amyloid β-protein, wherein the compound of formula I is prepared from the compound 6-bromo-2-(4-nitrophenyl)benzothiazole of formula II:

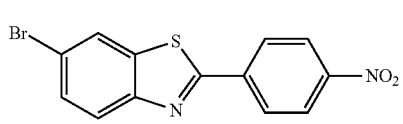

formula II

The compound capable of specifically binding to the amyloid β-protein of the formula I is 6-borono-2-(4-methyl aminophenyl)benzothiazole.

It is preferable that in the preparation process of the compound for specifically binding to the amyloid β-protein, the process for preparing 6-borono-2-(4-methyl aminophenyl)benzothiazole from 6-bromo-2-(4-nitrophenyl)benzothiazole including steps of:

reducing 6-bromo-2-(4-nitrophenyl)benzothiazole to obtain 6-bromo-2-(4-aminophenyl)benzothiazole;

reacting 6-bromo-2-(4-aminophenyl)benzothiazole and formaldehyde to obtain 6-bromo-2-(4-methyl aminophenyl) benzothiazole;

reacting 6-bromo-2-(4-methyl aminophenyl)benzothiazole and bis(pinacolato)diboron to obtain 2-(4-methyl aminophenyl)-6-(4,4,5,5-tetramethyl-1,3,2-dioxaborolan-2-yl) benzothiazole; wherein the boron in bis(pinacolato)diboron is $^{10}B$;

oxidizing 2-(4-methyl aminophenyl)-6-(4,4,5,5-tetramethyl-1,3,2-dioxaborolan-2-yl)benzothiazole by an oxidizing agent to obtain the compound 6-borono-2-(4-methyl aminophenyl)benzothiazole of formula I.

It is preferred that 6-borono-2-(4-methylaminophenyl)benzothiazole can also be prepared from 6-bromo-2-(4-nitrophenyl)benzothiazole including steps of:

reacting 6-bromo-2-(4-nitrophenyl)benzothiazole with bis(pinacolato)diboron to obtain 2-(4-nitrophenyl)-6-(4,4,5,5-tetramethyl-1,3,2-dioxaborolan-2-yl)benzothiazole; wherein the boron in bis(pinacolato)diboron is $^{10}B$;

oxidizing 2-(4-nitrophenyl)-6-(4,4,5,5-tetramethyl-1,3,2-dioxaborolan-2-yl)benzothiazole by an oxidizing agent to obtain 6-borono-2-(4-nitrophenyl)benzothiazole;

reducing 6-borono-2-(4-nitrophenyl)benzothiazole by a reducing agent to obtain 6-borono-2-(4-aminophenyl)benzothiazole;

reacting 6-borono-2-(4-aminophenyl)benzothiazole, methyl iodide and silver trifluoromethanesulfonate to obtain the compound 6-borono-2-(methylaminophenyl)benzothiazole of formula I.

In the above-mentioned two steps of synthesizing 6-borono-2-(4-methylaminophenyl)benzothiazole, the element $^{10}B$ of the compound of formula I is derived from the element $^{10}B$ of the reactant bis(pinacolato)diboron used. As described above, in preparing the compound of the formula I, the content of the $^{10}B$-containing bis(pinacolato)diboron in the reactant bis(pinacolato)diboron should be selected according to the purity of the $^{10}B$-containing compound required for practical application.

In addition, the element C in methyl iodide can be $^{12}C$ or $^{11}C$. It is further preferred that in the preparation process of the compound for specifically binding to the amyloid β-protein, the carbon in the methyl iodide is $^{11}C$. The 6-borono-2-(4-methylaminophenyl)benzothiazole synthesized from radioactive labeled methyl iodide is also radioactive and the radioactive $^{11}C$ is labeled on the methylamine group of $R_2$ of the compound of formula I.

The compound of formula I can be labeled with $^{11}C$ and used to track the part of amyloid β-protein deposition in the brain by using its radioactivity in combination with Positron Emission Computed Tomography (PET) for AD diagnosis. It should be noted that even if the compound of formula I is labeled with $^{11}C$, the compound still has a property of specifically binding to the amyloid β-protein, and the compound still contains a nuclide $^{10}B$ with large thermal neutron capture cross section. Therefore, the compound of formula I, which is labeled with $^{11}C$, still has a function for eliminating amyloid β-protein in the neutron capture therapy system.

It is preferred that in the preparation process of the compound for specifically binding to the amyloid β-protein, the oxidizing agent may preferably be sodium metaperiodate or other oxidizing agent having a similar oxidizing ability to sodium metaperiodate;

The third aspect of the present disclosure provides the use of 6-borono-2-(4-methylaminophenyl)benzothiazole in the preparation of a medicament for specifically binding to amyloid β-protein. The medicament prepared from 6-borono-2-(4-methyl aminophenyl)benzothiazole forms a conjugate with amyloid β-protein, and the conjugate is irradiated with neutron rays radiated by a neutron capture therapy device. The neutrons and $^{10}B$ elements react to produce energy that destroys amyloid β-protein.

The fourth aspect of the present disclosure provides the use of $^{11}C$-labeled 6-borono-2-(4-methylaminophenyl)benzothiazole in the preparation of a PET imaging agent for amyloid β-protein.

The beneficial effects of the present disclosure are, on the one hand, by providing a novel compound capable of specifically binding to amyloid β-protein, to achieve the elimination of amyloid β-protein that specifically binds to the compound by means of a neutron capture therapy device, providing a new way of idea and process to eliminate amyloid β-protein; on the other hand, by providing a 6-borono-2-(4-methyl aminophenyl)benzothiazole labeled with radioisotope $^{11}C$, to provide a new choice for the PET imaging agent for amyloid β-protein.

Figure 4:
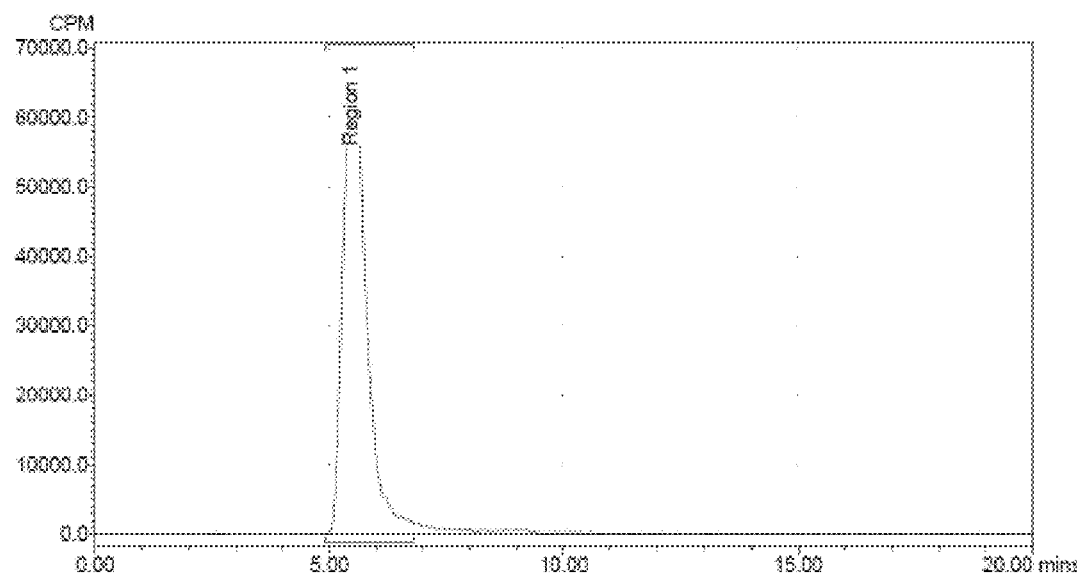
Figure 4:
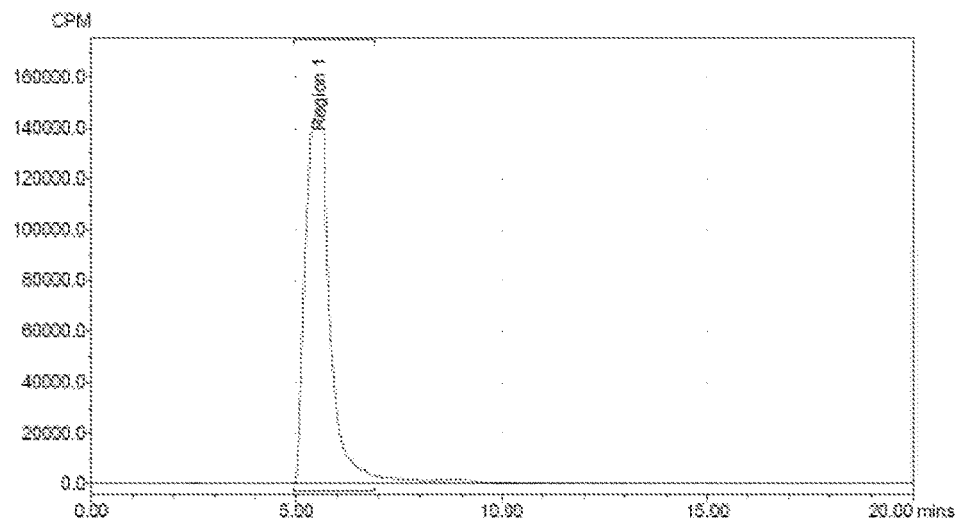
Figure 5:
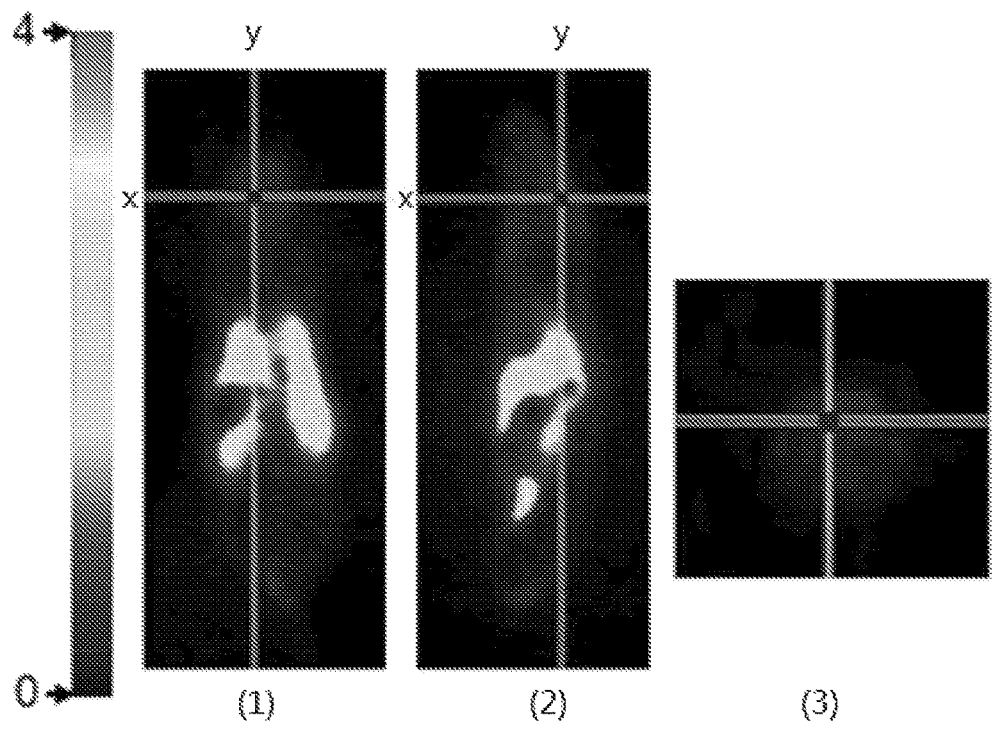
Figure 5:
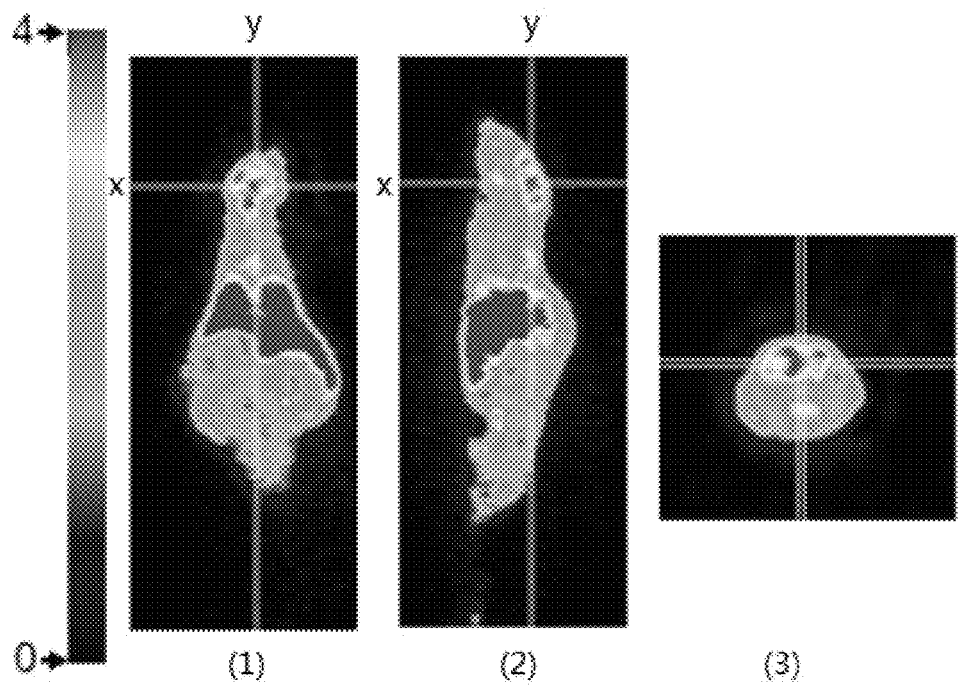

Graphs (1) and (2) in FIG. 4 are the stability spectrum of $^{11}C$-labeled 6-borono-2-(4-methylaminophenyl)benzothiazole at 30 min and 60 min, respectively;

Graphs A and B in FIG. 5 are PET images of the control and SAMP8 model mice at 30 minutes after the injection of labelled 2-(4-methyl aminophenyl)-6-dihydroxyboroobenzothiazole, respectively.

Figure 6:
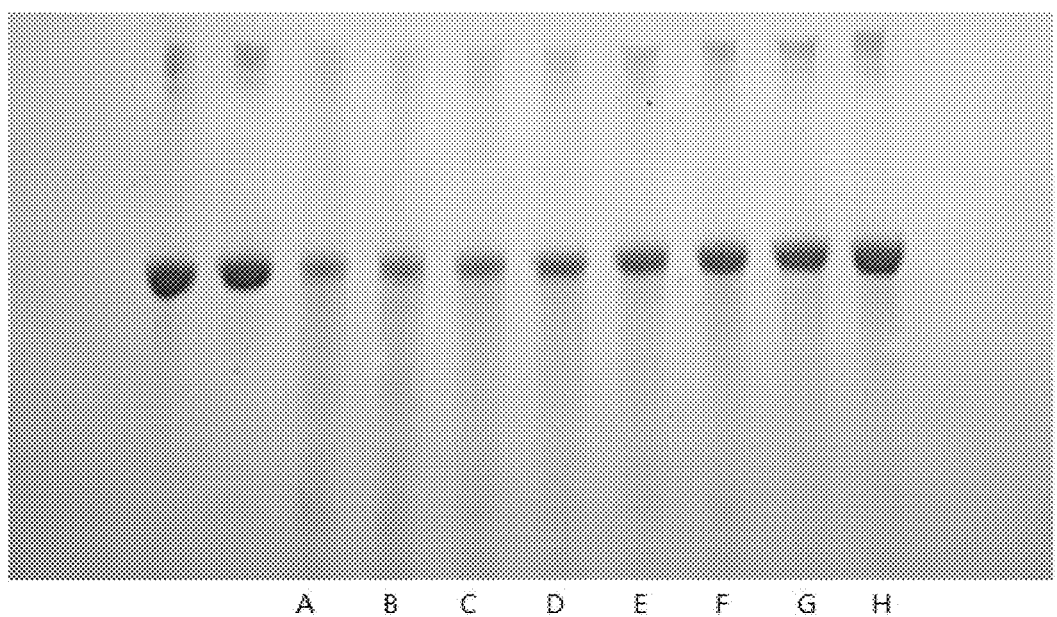

FIG. 6 is an SDS-PAGE electrophoresis pattern of the mixed solution of bovine serum albumin and $H_3{}^{10}BO_3$ irradiated with radiation at different positions from the exit of the collimator, respectively.

DETAILED DESCRIPTION

The present disclosure will now be described in further detail with reference to the accompanying drawings in order to enable those skilled in the art to implement with reference to the teachings.

It is to be understood that the terms "having", "comprising", "including" as used herein do not exclude the presence or addition of one or more other ingredients or combinations thereof.

The fast neutrons herein neutrons with energy range of greater than 40 keV, epithermal neutron with energy range of 0.5 eV to 40 keV, and thermal neutron with energy range of less than 0.5 keV.

Figure 1:
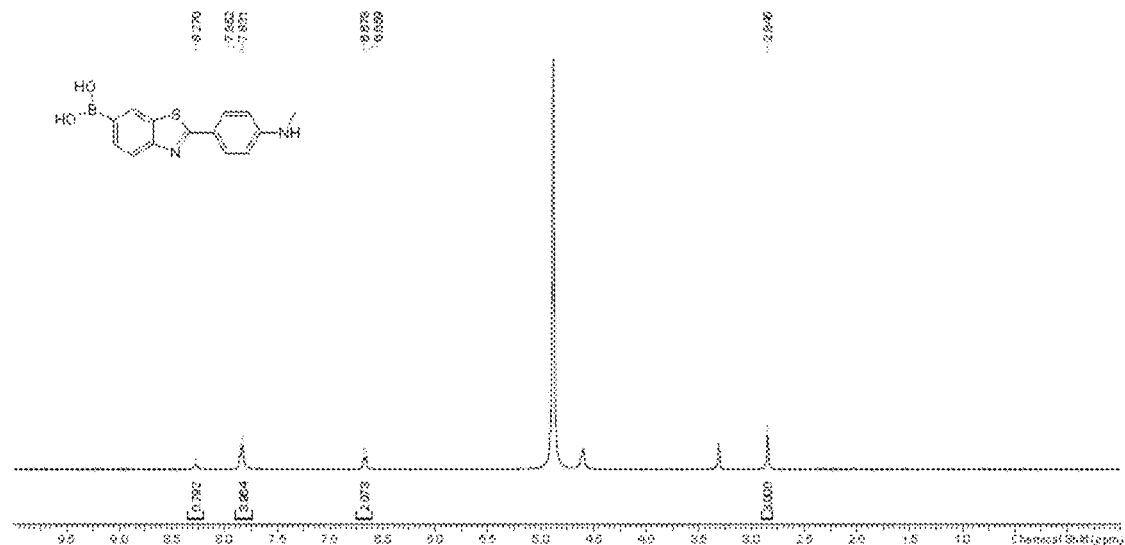
FIG. 1 is a $^1H$ NMR spectrum of 6-borono-2-(4-methylaminophenyl)benzothiazole.

The compound for specifically binding to amyloid β-protein provided by the present disclosure is 6-borono-2-(4-methylaminophenyl)benzothiazole, and the structure thereof is confirmed as shown in FIG. 1. The compounds can be combined with a neutron capture therapy device to eliminate amyloid β-protein deposition plaques.

Figure 2:
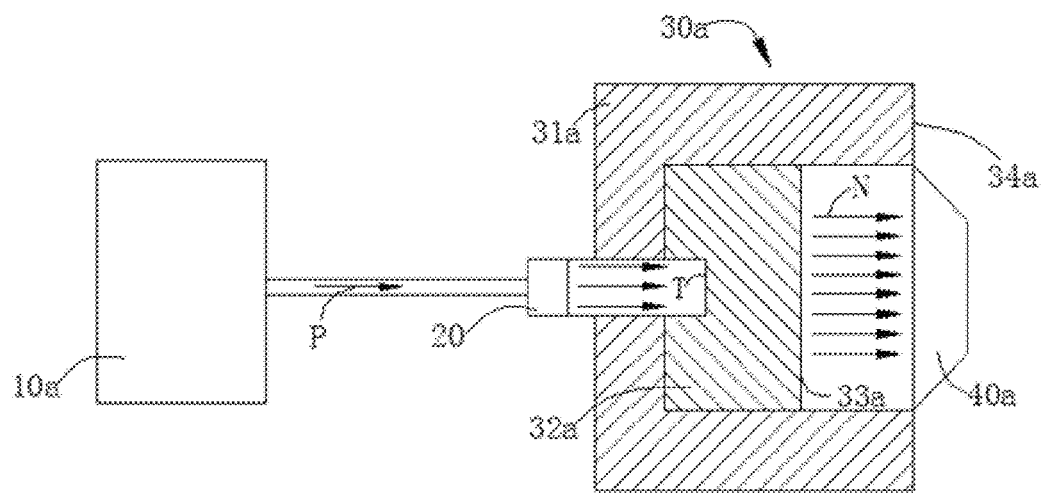
FIG. 2 is a schematic plan view of a neutron capture therapy device for an accelerator neutron source.
Figure 3:
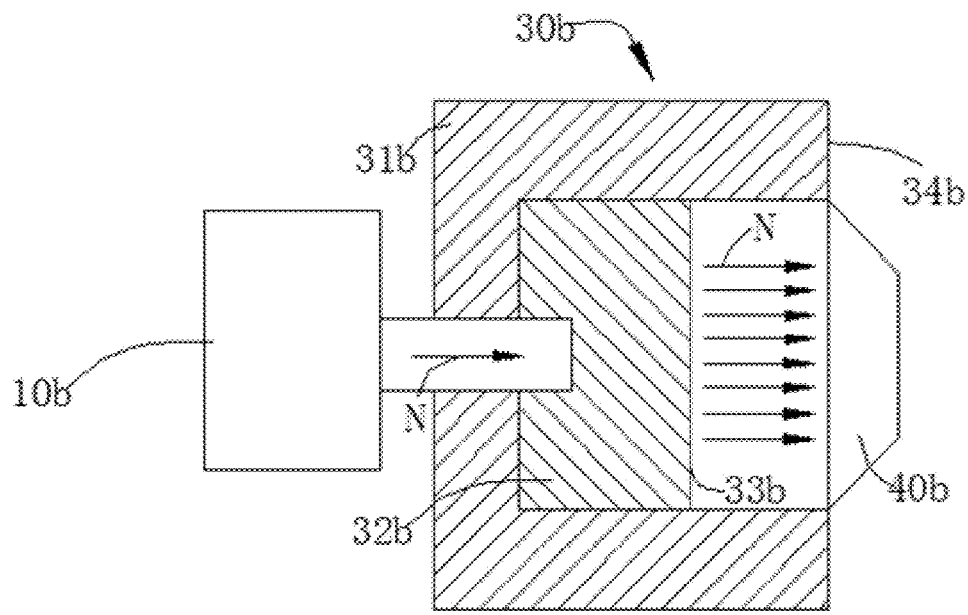
FIG. 3 is a schematic plan view of a neutron capture therapy device for a reactor neutron source.

As shown in FIG. 2 or FIG. 3, the neutron capture therapy device includes a neutron source, a beam shaping assembly and a collimator, wherein the beam shaping assembly includes a reflector, a moderator, a thermal neutron absorber and a radiation shielding means, wherein the neutron source includes an accelerator-based neutron source and a reactor-based neutron source.

In the practical application of the neutron capture therapy system to eliminate amyloid β-protein, it is usually necessary to adjust the fast neutrons in the mixed radiation field to the superheat neutrons and reduce the amount of other harmful rays in the mixed radiation field in the beam shaping of the neutron capture therapy device. In the practical application of the neutron capture therapy system to eliminate amyloid β-protein, it is usually necessary to adjust the fast neutrons in the mixed radiation field to the epithermal neutrons and reduce the amount of other harmful rays in the mixed radiation field in the beam shaping assembly of the neutron capture therapy device. However, considering that in the process of neutron beam travelling from the collimator of the neutron capture therapy device to a compound that specifically binds to the amyloid β-protein, the energy of the neutron beam will have a certain degree of attenuation as the distance between the two increases, and in the process for the neutron beam to arrive at the compound that specifically binds to the amyloid β-protein, there are often other substances moderating the energy of the neutrons in varying degrees, thus, in order to ensure the energy and neutron intensity of the neutrons arriving at the compound that specifically binds to the amyloid β-protein, it is usually necessary to slow the fast neutrons in the beam shaping assembly to epithermal neutrons and to increase the amount of epithermal neutrons in the neutron beam coming out of the collimator.

Referring again to FIG. 2, the neutron capture therapy device in the neutron capture therapy system is a neutron capture therapy device for the accelerator neutron source, wherein the accelerator 10a accelerates the proton, expands the cross-sectional area of the proton beam P by the beam expander 20, causes the proton beam P to hit the target T and generate neutrons. The reaction principle is that the charged particles such as proton and deuteron are accelerated by the accelerator to energy enough to overcome the target nucleus Coulomb repulsion, and carry out a nuclear reaction with the metal target T producing nuclei and neutrons, wherein, the commonly used metal targets are usually lithium and beryllium. By this method, a mixed radiation field is generated, when acting on amyloid β-protein 53 using the neutron capture therapy device, it is necessary to reduce the other kinds of rays as much as possible. And the moderator 32a in the beam shaping assembly 30a has the effect of adjusting the energy of the mixed radiation field, and the reflector 31a reflects the mixed radiation field diffused in the other direction to reduce the loss of the neutron. The beam shaping assembly 30a may also include a thermal neutron absorber 33a capable of absorbing lower energy of the thermal neutrons. The beam shaping assembly 30a is provided with a radiation shielding means 34a outside to prevent the radiation from causing damage to the nearby person. The collimator 40a is mounted at the rear of the beam shaping assembly 30a, and the beam after adjustment by the beam shaping assembly 30a is then converged by the collimator 40a to more accurately irradiate the compound 52 containing the nuclide 51 with a large thermal neutron capture cross section and capable of specifically binding to the amyloid β-protein 53. The epithermal neutron beam is more fully utilized.

Referring again to FIG. 3, the neutron capture therapy device in the neutron capture therapy system is a neutron capture therapy device for the reactor neutron source, wherein the reactor neutron source 10b passes the generated neutron beam N to the beam shaping assembly 30b through a pipe. Both the reactor neutron source 10b and the neutron source of the accelerator 10a generate a mixed radiation field. The fast neutrons having a high energy in the mixed radiation field are slowed by the moderator 32b in the beam shaping assembly 30b to neutrons that can destroy the structure of amyloid β-protein. The rays diffused in the other directions are reflected back into the moderator 32b through the reflector 31b to improve the utilization of the radiation. The thermal neutron absorber 33b in the beam shaping assembly can absorb the lower thermal neutrons in the mixed radiation field so that the epithermal neutron content in the neutron beam N is higher. The neutron beam N, after the convergence of the collimator 40b, can be used to more accurately irradiate the compound 52 containing the nuclide 51 with a large thermal neutron capture cross section and capable of specifically binding to the pathogenic protein 53. The epithermal neutron beam is more fully utilized.

The technical solutions of the present disclosure will be further described with reference to the following examples.

The compounds that specifically binds to amyloid β-protein described in the preferred embodiments of the present disclosure refer to 6-borono-2-(4-methylaminophenyl)benzothiazole, wherein the boron element on the compound is $^{10}B$ and the compound may contain a radioactive element $^{11}C$. The boron elements in the boron-containing compounds described in the preferred embodiments of the present disclosure contain $^{10}B$, unless otherwise specified.

Example 1 Preparation of a Compound that Specifically Binds to Amyloid β-Protein The compound 6-borono-2-(4-methylaminophenyl)benzothiazole of the formula I can be prepared by steps of:

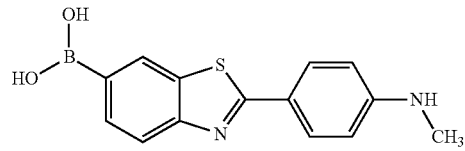

formula I 1 g of 6-bromo-2-(4-nitrophenyl)benzothiazole was dissolved in 10 mL of ethanol and 5.39 g of $SnCl_2.2H_2O$ was added. The reaction was stirred at 100° C. for 1 h to obtain 6-bromo-2-(4-aminophenyl)benzothiazole;

$^1$H NMR: 400 MHz DMSO

δ 8.29 (s, 1H), 7.80-7.82 (d, J=8.8 Hz, 1H), 7.74-7.76 (d, J=8.8 Hz, 2H), 7.58-7.60 (m, 1H), 6.65-6.67 (d, J=8.4 Hz, 2H), 5.95 (s, 2H).

To 1 g of 6-bromo-2-(4-aminophenyl)benzothiazole was added 16.4 mmol of formaldehyde, 10 mL of tetrahydrofuran (THF) and 20 mL of methanol were added thereto, and 0.886 g of sodium methoxide was added in one portion, and the reaction solution was stirred at 65° C. for 12 h, and then was cooled to 25° C., 620.41 mg of sodium borohydride (NaBH$_4$) was added and the reaction temperature was raised to 65° C. The reaction was stirred for 1 h to obtain 6-bromo-2-(4-methylaminophenyl)benzothiazole;

$^1$H NMR: 400 MHz CDCl$_3$

δ 7.97 (s, 1H), 7.89-7.91 (d, J=8.8 Hz, 2H), 7.81-7.83 (d, J=8.8 Hz, 1H), 7.52-7.54 (m, 1H), 6.64-6.66 (d, J=8.8 Hz, 2H), 2.93 (s, 3H).

A reaction system consisted of 100 mg of 6-bromo-2-(4-methylaminophenyl)benzothiazole, 95.46 mg of bis(pinacolato)diboron and 92.23 mg of potassium acetate. To the reaction system was added 4 mL of THF and 2 mL of dimethylsulfoxide (DMSO). 26.39 mg of dichlorobis (triphenylphosphine) palladium (Pd(PPh$_3$)$_2$Cl$_2$) was added under nitrogen at 20° C. and the reaction was stirred at 90° C. for 12 h to obtain 2-(4-methyl aminophenyl)-6-(4,4,5,5-tetramethyl-1,3,2-dioxaborolan-2-yl)benzothiazole, wherein the boron in the bis(pinacolato)diboron includes $^{10}$B;

$^1$H NMR: 400 MHz MeOH

δ 8.26 (s, 1H), 7.82-7.86 (m, 4H), 7.76-7.93 (m, 2H), 4.07 (s, 1H), 2.63 (s, 3H), 1.2 (s, 12H).

300 mg of 2-(4-methyl aminophenyl)-6-(4,4,5,5-tetramethyl-1,3,2-dioxaborolan-2-yl) benzothiazole was added to 20 mL of THF and 10 mL of water, and then 875.93 mg of sodium metaperiodate (NaIO$_4$) was added to form a reaction system. The reaction system was stirred at 25° C. for 12 h to obtain the compound of formula I: 6-borono-2-(4-methylaminophenyl)benzothiazole. The $^1$H NMR scan spectrum of the compound is shown in FIG. 1.

$^1$H NMR: 400 MHz MeOH

δ 8.27 (s, 1H), 7.83-7.85 (m, 4H), 6.66-6.68 (d, J=7.6 Hz, 2H), 2.85 (s, 3H).

Wherein, 6-bromo-2-(4-nitrophenyl)benzothiazole can be prepared by steps of:

5 g of 6-bromo-2-amino-benzothiazole was added to 25 mL of a solution of potassium hydroxide at a concentration of 10 M, and then 5 mL of ethylene glycol was added to form a mixed solution which was stirred at 125° C. for 2 h to obtain 2-amino-bromophenyl mercaptan;

$^1$H NMR: 400 MHz DMSO

δ 7.21-7.26 (m, 1H), 6.99 (s, 1H), 6.81-6.72 (m, 1H), 6.39 (s, 1H), 5.72 (s, 2H).

1.48 g of p-nitrobenzaldehyde was added to 2 g of 2-amino-5-bromophenyl mercaptan, and then 40 mL of DMSO was added to form a reaction solution, which was stirred at 180° C. for 0.5 h to obtain 6-bromo-2-(4-nitrophenyl)benzothiazole;

$^1$H NMR: 400 MHz DMSO

δ 8.54 (s, 1H), 8.34-8.41 (m, 4H), 8.07-8.09 (d, J=8.8 Hz, 1H), 7.74-7.77 (m, 1H).

The specific reaction procedure for the synthesis of 6-borono-2-(4-methylaminophenyl)benzothiazole in this example is shown in Scheme II (The boron element in the scheme includes $^{10}$B):

Scheme II

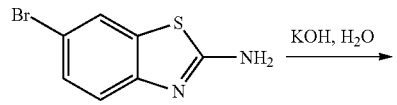

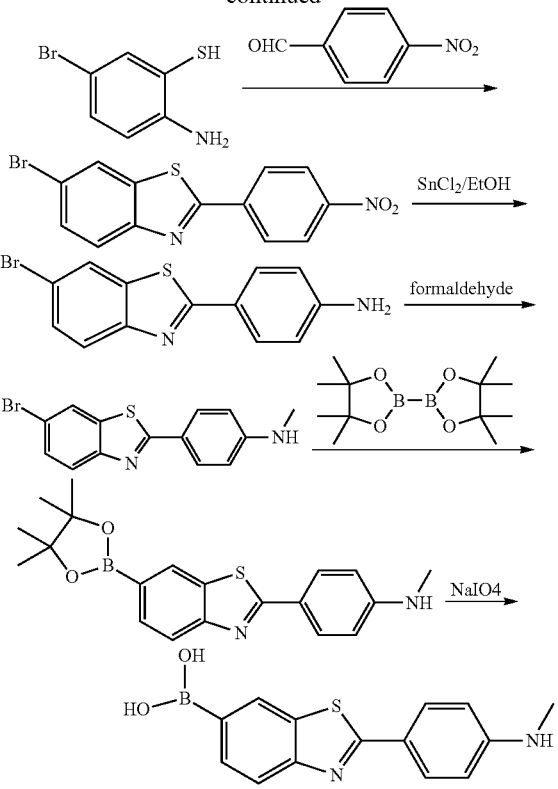

Example 2 Preparation of a Compound that Specifically Binds to Amyloid β-Protein The synthesis method of 6-bromo-2-(4-nitrophenyl)benzothiazole in this example is the same as that shown in Example 1.

To 100 mg of 6-bromo-2-(4-nitrophenyl)benzothiazole was added 90.91 mg of bis(pinacolato)diboron and 87.84 mg of potassium acetate, then, 4 mL of THF and 2 mL of DMSO was added, and 25 mg of dichlorobis (triphenylphosphine) palladium was added under nitrogen at 20° C., and the reaction system was stirred at 95° C. for 15 h to obtain 2-(4-nitrophenyl)-6-(4,4,5,5-tetramethyl-1,3,2-dioxaborolan-2-yl)benzothiazole, wherein the boron in the bis(pinacolato)diboron includes $^{10}$B.

$^1$H NMR: 400 MHz CDCl$_3$

δ 8.44 (s, 1H), 8.35-8.37 (d, J=8.8 Hz, 2H), 8.28-8.30 (d, J=8.8 Hz, 2H), 8.11-8.13 (d, J=8 Hz, 1H), 7.96-7.98 (d, J=8 Hz, 1H), 1.40 (s, 12H).

To 539.7 mg of 2-(4-nitrophenyl)-6-(4,4,5,5-tetramethyl-1,3,2-dioxaborolan-2-yl)benzothiazole was added 30 mL of THF and 10 mL of water, followed by the addition of 1.51 g of sodium metaperiodate, the reaction system was reacted at 25° C. for 23 h to obtain 6-borono-2-(4-nitrophenyl)benzothiazole;

$^1$H NMR: 400 MHz DMSO

δ 8.56 (s, 1H), 8.36-8.42 (m, 4H), 8.29 (m, 2H), 8.10-8.12 (d, J=8.4 Hz, 1H), 8.00 (m, 1H).

To 100 mL of methanol was added 200 mg of catalyst Pd/C, and then 180 mg of 6-borono-2-(4-nitrophenyl)benzothiazole was added to form a reaction system, the reaction system was vacuum degassed in a hydrogen atmosphere and reacted at 25° C. for 10 min to obtain 6-borono-2-(4-aminophenyl)benzothiazole;

1H NMR: 400 MHz MeOH

δ 8.29 (s, 1H), 7.80-7.84 (m, 4H), 6.74-6.76 (d, J=8.8 Hz, 2H).

Methyl iodide was carried by nitrogen to pass through a silver trifluoromethanesulfonate tube heated to 200° C., and then passed into anhydrous acetone in which 6-borono-2-(4-aminophenyl)benzothiazole was dissolved to form a reaction solution, the reaction solution was reacted at 80° C. for 5 min and quenched with water to obtain 6-borono-2-(4-methylaminophenyl)benzothiazole.

Wherein the element C in the methyl iodide may be a radioactive $^{11}$C, thus, 6-borono-2-(4-methylaminophenyl) benzothiazole synthesized from it also has a radioactive element $^{11}$C, therefore, the radioactive compound can be used in conjunction with PET to track the site of amyloid β-protein deposition in the brain and the diagnosis of AD.

1H NMR: 400 MHz MeOH

δ 8.27 (s, 1H), 7.83-7.85 (m, 4H), 6.66-6.68 (d, J=7.6 Hz, 2H), 2.85 (s, 3H).

The reaction procedure of this example is shown in Scheme III (The boron element in the scheme includes $^{10}$B):

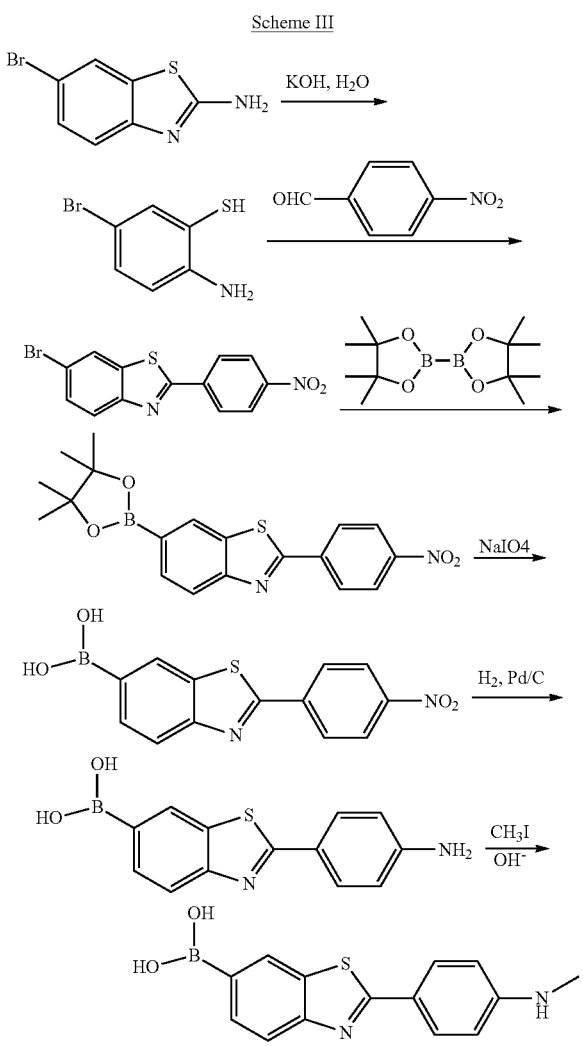

Scheme III

Example 3 Use of 6-Borono-2-(4-Methylaminophenyl)Benzothiazole in the Preparation of a PET Imaging Agent for Amyloid β-Protein By an experimental method well known to those skilled in the art, the 6-borono-2-(4-methylaminophenyl)benzothiazole labeled with synthesized in Example 2 was purified by preparative HPLC to give a radioactive chemical purity of 98.15%, with a retention time of 5.43 min, which was consistent with the retention time of the standard sample of 6-borono-2-(4-methylaminophenyl)benzothiazole, thus the purified product was confirmed to be the desired radioactive compound.

The stability of $^{11}$C-labeled 6-borono-2-(4-methylaminophenyl)benzothiazole in vitro was determined by HPLC, at selected time of 30 min and 60 min. In FIG. 4, graph (1) shows the radioactivity spectrum of stability for 30 min, (2) the radioactivity spectrum of stability for 60 min, and radioactive chemical purity at 30 min and 60 min were both 100%. Therefore, the radioactive chemical purity of the $^{11}$C-labeled radioactive compound met the experimental requirements.

Example 4 Experiment of $^{11}$C-Labeled 6-Borono-2-(4-Methylaminophenyl)Benzothiazole Specifically Binding to Amyloid β-Protein SAMP8 (senescence accelerated mouse prone 8) mice are the most common animal model of AD (Alzheimer's disease), in its brain there are a large number of amyloid deposition plaque. In this example, SAMP8 mice were used as model mice, and the normal mice were used as the control mice. Both the model mice and the control mice were 10 months old. The two mice were injected with 6-borono-2-(4-methylaminophenyl)benzothiazole containing $^{11}$C labeling, and the Micro-PET scan is used to study whether 6-borono-2-(4-methylaminophenyl)benzothiazole and amyloid β-protein have specific binding properties. Model mice and control mice weighing 31.5±0.3 g were selected, 31.0±0.6 μCi of $^{11}$C labelled 6-borono-2-(4-methyl aminophenyl)benzothiazole were injected thereto, and Micro-PET of Model INVEON from Siemens were used for scan, where the scanning window was 350-650 KeV.

It is well known to those skilled in the art that the major cause of Alzheimer's disease is that the amyloid β-protein deposition plaques accumulate in the cerebral cortex and hippocampus of the brain. In this example, Micro-PET scanned and compared the brains of the model and control mice using PMOD software. And the absorption of radioactive 6-borono-2-(4-methylaminophenyl)benzothiazole in the cerebral cortex and hippocampus of SAMP8 model mice and control mice was determined, to further illustrate that the compound is capable of specifically binding to amyloid β-protein deposition plaques. The specific results are shown in Table 1 and Table 2:

TABLE 1

The uptake of radioactive
6-borono-2-(4-methylaminophenyl)benzothiazole
in cerebral cortex of model mice and control mice

| Time after radiopharmaceutical injection (min) | Cerebral cortex uptake of radiopharmaceuticals (% ID/g) | | Ratio (model mice/control mice) |
|---|---|---|---|
| | Model mice | Control mice | |
| 5 | 3.03 | 1.61 | 1.9 |
| 15 | 2.88 | 1.48 | 1.9 |
| 25 | 2.79 | 1.17 | 2.4 |
| 35 | 2.68 | 0.99 | 2.7 |

As can be seen from Table 1: 35 minutes after the injection of radiopharmaceuticals, the cerebral cortex uptake ratio of the model mice to the control mice was 2.7, higher than the boron ratio (2.5) of the target and the non-target in the effective boron neutron capture therapy. The results suggest that radioactive 6-borono-2-(4-methylaminophenyl)benzothiazole can be effectively bound to the amyloid β-protein deposition plaque and accumulate at the lesion. It is more desirable for the patients with Alzheimer's disease treated with boron neutron capture therapy, the lesions can accept a large number of radiation dose, to achieve the purpose of treatment, and reduce the radiation damage to the normal brain tissue.

TABLE 2

The uptake of radioactive 6-borono-2-
(4-methylaminophenyl)benzothiazole in hippocampus of model mice and
control mice

| Time after radiopharmaceutical injection (min) | hippocampus uptake of radiopharmaceuticals (% ID/g) | | Ratio (model mice/control mice) |
|---|---|---|---|
| | Model mice | Control mice | |
| 5 | 3.44 | 1.80 | 1.9 |
| 15 | 3.50 | 1.49 | 2.3 |
| 25 | 3.45 | 1.09 | 3.2 |
| 35 | 3.27 | 1.01 | 3.2 |

As can be seen from Table 2, 25 and 35 minutes after the injection of radiopharmaceuticals, the hippocampus ratio of the model mice to the control mice was 3.2, higher than the boron ratio (2.5) of the target and the non-target in the effective boron neutron capture therapy. The results also suggest that radioactive 6-borono-2-(4-methylaminophenyl)benzothiazole can be effectively bound to the amyloid β-protein deposition plaque and accumulate at the lesion.

SAMP8 model mice are accelerated aging mice with Alzheimer's disease, and a large number of amyloid β-protein deposition plaque are accumulated in the cerebral cortex and hippocampus lesions. It can be seen from the experimental data of the model mice and the control mice in Table 1 and Table 2 that the cerebral cortex and hippocampus of the SAMP8 model mice have a stronger ability to absorb 6-borono-2-(4-methylaminophenyl)benzothiazole compared to the normal control mice. It is also further explained that 6-borono-2-(4-methylaminophenyl)benzothiazole is specific for amyloid β-protein are specific, and boron neutron capture therapy can be used in the future to treat Alzheimer's disease and provide another advanced treatment for patients with Alzheimer's disease.

According to the results of the analysis of Table 2, 25 to 35 minutes after the injection of radioactive 6-borono-2-(4-methylaminophenyl)benzothiazole in mice, the ratio of radiopharmaceuticals in the hippocampus of the model mice and mice was 3.2. Thus, the Micro-PET image of the intermediate value of 30 minutes was used to further compare the accumulation of the radioactivity of 6-borono-2-(4-methylaminophenyl)benzothiazole in the brain.

FIG. 5 is an image of PET scan and processed by AMIDE software at 30 min after the injection of radioactive 6-borono-2-(4-methylaminophenyl)benzothiazole, wherein graph A is the image of the control mice injected with radiopharmaceutical at 30 min, in graph A, picture (1) shows the scan image of coronal section of the control mouse, picture (2) is a cross-sectional view of picture (1) along the Y-axis, picture (3) is a brain cross-sectional view of picture (1) along the Y-axis; graph B is the image of the SAMP8 model mice injected with radiopharmaceutical at 30 min, similarly, in graph B, picture (1) shows the scan image of coronal section of the control mouse, picture (2) is a cross-sectional view of picture (1) along the Y-axis, picture (3) is a brain cross-sectional view of picture (1) along the Y-axis.

Wherein picture (3) of graph A and picture (3) of graph B can reflect the brain radiopharmaceutical absorption. It can be seen from comparison of these two images, the brain of the SAMP8 model mouse in graph B (3) has accumulated a large amount of radiopharmaceuticals relative to the brain of the control mice in graph A (3), and it is already known that the model mouse brain has a large number of amyloid β-protein deposition plaques, it can be explained that 6-borono-2-(4-methylaminophenyl)benzothiazole is specific for amyloid β-protein deposition plaque, and in the future 6-borono-2-(4-methyl aminophenyl)benzothiazole can be used for boron neutron capture therapy.

Example 5 Experiment for Simulation of the Neutron Capture Therapy System to Eliminate Protein In this example, boronic acid ($H_3^{10}BO_3$) was used in place of 6-borono-2-(4-methyl aminophenyl)benzothiazole, wherein the boron element in boric acid ($H_3^{10}BO_3$) was $^{10}B$, and bovine serum albumin (BSA) was used to mimic amyloid β-protein. The mixed solution of boric acid and bovine serum albumin was placed in a neutron beam capture environment. The effect of neutron on bovine serum albumin and the effect of neutron on bovine serum albumin in the presence of $H_3^{10}BO_3$ were analyzed by SDS-PAGE gel electrophoresis.

Effect of Neutron on Bovine Serum Albumin

A BSA solution of concentration of 0.01% (w/w) was prepared with ultrapure water, and the prepared solution was stored and operated at 4° C. A 1 mL BSA solution was placed on the centerline of the exit of the collimator of the neutron capture therapy device, wherein the distance of the solution from the exit of the collimator was 2 cm and a neutron capture therapy device was arranged so that the neutron intensity at the exit of the collimator was $2.4*10^{11}$/s, and the BSA solution was irradiated in the neutron environment for 2 h; another 1 mL BSA solution was taken as a control solution without neutron irradiation.

The BSA solution with neutron irradiation for 2 h and the control solution were stained with Coomassie brilliant blue and subjected to SDS-PAGE gel electrophoresis, the colors of the protein bands in the electrophoresis pattern of the sample solution and the control solution were quantified by Image J software, and the values were used to represent the relative content of protein, wherein the content of BSA in the control solution was defined as 1. Under the above neutron irradiation experiment, the content of BSA after the neutron irradiation for 2 h was 0.8, and its content was reduced by about 20%. It can be seen that the radiation containing the neutron beam can affect the protein content.

II. Effect of Neutron on Bovine Serum Albumin in the Presence of $H_3{}^{10}BO_3$ A solution of BSA and $H_3{}^{10}BO_3$ was prepared with ultrapure water, wherein in the solution, the concentration of BSA was 0.01% (w/w), and the concentration of $H_3{}^{10}BO_3$ was 0.18 M; and the prepared solution was stored and operated at 4° C. 8 parts (numbered A, B, C, D, E, F, G, H, respectively) were taken from the solution, and 1 mL of each solution was irradiated with a neutron capture therapy device. 8 parts of the solution were respectively placed on the center line of the exit of the collimator of the neutron capture therapy device, Solution A was 2 cm from the exit of the collimator, Solution B was 4 cm from the exit of the collimator, Solution C was 6 cm from the exit of the collimator, and so on. The beam at the exit of the collimator, in addition to the neutron beam, also includes gamma rays and other radiation, mainly neutron rays that actually destroy the protein. The example described the intensity of the beam with the neutron intensity in the beam, wherein, the neutron strength used in the present example was $2.4*10^{11}$/s, and 8 parts of the solution were irradiated for 2 h in the neutron environment; and another 1 mL of the BSA and $H_3{}^{10}BO_3$ solution was used as a control solution without neutron irradiation.

The control solution and the 8 parts of the solution irradiated by the radiation of the neutron capture therapy device were stained with Coomassie Brilliant Blue and subjected to SDS-PAGE gel electrophoresis. FIG. 6 shows the SDS-PAGE electrophoresis pattern of the control solution and the 8 parts of the solution.

The first two protein bands in FIG. 6 were BSA in the control solution and the rest were BSA after exposure to the radiation. 8 parts of the solution were placed on the center line of the exit of the collimator. Since the solutions on the center line all contain $H_3{}^{10}BO_3$ and the $^{10}B$ element has a large thermal neutron capture cross section, the neutron dose decreased significantly after the neutrons in the radiation from the exit of the collimator were passed through the solution containing $H_3{}^{10}BO_3$. The farther away from the collimator, the less the neutron radiation dose received by the BSA.

As can be seen from FIG. 6, the colors of the protein bands of the eight neutron-irradiated solution became lighter in different degrees compared to that of the control. And the closer to the exit of the collimator, the lighter the color of the protein bands in the solutions, indicating the more the protein content was reduced, and the closer to the exit of the collimator, the greater the neutron radiation dose received by the solution. It is further explained that the size of the neutron dose affects the content of BSA in the solution, and the stronger the neutron dose, the less the content of BSA in the solution after the neutron irradiation.

The colors of the BSA protein bands in the electrophoresis patterns corresponding to the control solution and 8 parts of the solution were quantified by Image J software, and the values were used to represent the relative content of the protein, wherein the content of BSA in the control solution was defined as 1. Under the above neutron irradiation experiment, the contents of BSA after neutron irradiation for 2 h are shown in Table 3.

It can be seen from Table 3, the content of BSA in the solution irradiated by neutrons decreased to varying degrees. After 2 hours of neutron irradiation with a neutron intensity of $2.4*10^{11}$/s on the solution placed at 2 cm from the exit of the collimator, the BSA content thereof was only 5.3%, indicating that the neutron can greatly destroy the structure of BSA and decrease the content of BSA in the presence of $H_3{}^{10}BO_3$. And within the allowable range of experimental error, among the 8 solutions, the farther distance of the solution from the exit of the collimator, the BSA contents as a whole showed a decreasing trend, further indicating that the size of the neutron dose affected the BSA content.

TABLE 3 effect of neutron on bovine serum albumin in the presence of $H_3{}^{10}BO_3$

| Solution number | BSA content (%) |
| --- | --- |
| Control solution | 100 |
| A | 5.3 |
| B | 2.6 |
| C | 18.9 |
| D | 14.0 |
| E | 22.9 |
| F | 35.1 |
| G | 49.6 |
| H | 60.7 |

The compound 6-borono-2-(4-methylaminophenyl)benzothiazole provided by the present disclosure carry a nuclide $^mB$ with a large thermal neutron capture cross section as $H_3{}^{10}BO_3$ and capable of specifically binding to the amyloid β-protein. The compound is placed in an environment containing amyloid β-protein, and the compound will form a high concentration around the amyloid β-protein. Then the region where the compound accumulates is irradiated with neutron beam emitted by a neutron capture therapy device, and the energy released can destroy the structure of the protein.

While the present disclosure has been described in detail with reference to specific embodiments thereof, it is to be noted that the above embodiments are provided for the purpose of further explanation of the disclosure and are not representative of the scope of the disclosure, that non-essential modifications and adjustment made by others in accordance with the teachings of the present disclosure is still within the scope of the present disclosure.

What is claimed is:

1. A compound for specifically binding to amyloid β-protein, wherein the compound has a structure as shown in formula I:

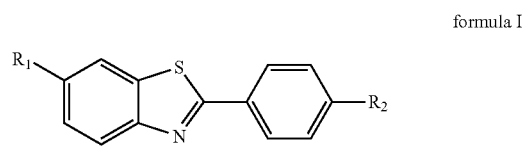

formula I wherein $R_1$ is —$B(OH)_2$, $R_2$ is —$NHCH_3$; and
wherein the boron element in $R_1$ is a nuclide $^{10}B$ with a large thermal neutron capture cross section.

2. The compound for specifically binding to amyloid β-protein according to claim 1, wherein the carbon element in $R_2$ of the compound is $^{11}C$.

3. A process for preparing the compound according to claim 1, wherein the compound for specifically binding to amyloid β-protein is prepared from compounds selected from the group consisting of:

formula II:

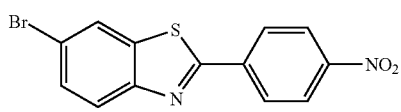

formula II the compound of formula II is 6-bromo-2-(4-nitrophenyl) benzothiazole;

formula A:

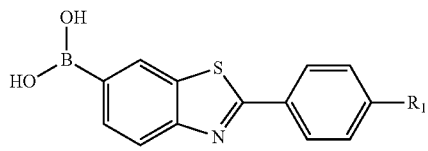

formula A wherein $R_1$ is —$NO_2$ or —$NH_2$,
when $R_1$ is —$NO_2$, the compound is 6-borono-2-(4-nitrophenyl)benzothiazole;
when $R_1$ is —$NH_2$, the compound is 6-borono-2-(4-aminophenyl)benzothiazole;

formula X:

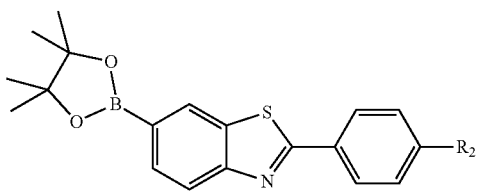

formula X wherein $R_2$ is —$NO_2$ or —$NHCH_3$,
when $R_2$ is —$NO_2$, the compound is 2-(4-nitrophenyl)-6-(4,4,5,5-tetramethyl-1,3,2-dioxaborolan-2-yl)benzothiazole;
when $R_2$ is —$NHCH_3$, the compound is 2-(4-methylaminophenyl)-6-(4,4,5,5-tetramethyl-1,3,2-dioxaborolan-2-yl)benzothiazole.

4. The process according to claim 3, wherein the process for preparing the compound for specifically binding to amyloid β-protein from the compound of formula II comprises steps of:
reducing 6-bromo-2-(4-nitrophenyl)benzothiazole to obtain 6-bromo-2-(4-aminophenyl)benzothiazole;
reacting 6-bromo-2-(4-aminophenyl)benzothiazole and formaldehyde to obtain 6-bromo-2-(4-methyl aminophenyl)benzothiazole;
reacting 6-bromo-2-(4-methyl aminophenyl)benzothiazole and bis(pinacolato)diboron to obtain 2-(4-methyl aminophenyl)-6-(4,4,5,5-tetramethyl-1,3,2-dioxaborolan-2-yl)benzothiazole;
oxidizing 2-(4-methyl aminophenyl)-6-(4,4,5,5-tetramethyl-1,3,2-dioxaborolan-2-yl)benzothiazole by an oxidizing agent to obtain the compound 6-borono-2-(4-methyl aminophenyl)benzothiazole of formula I;
wherein the boron in bis(pinacolato)diboron is $^{10}B$.

5. The process according to claim 3, wherein the process for preparing the compound for specifically binding to amyloid β-protein from the compound of formula II comprises steps of:
reacting 6-bromo-2-(4-nitrophenyl)benzothiazole with bis(pinacolato)diboron to obtain 2-(4-nitrophenyl)-6-(4,4,5,5-tetramethyl-1,3,2-dioxaborolan-2-yl)benzothiazole;
oxidizing 2-(4-nitrophenyl)-6-(4,4,5,5-tetramethyl-1,3,2-dioxaborolan-2-yl)benzothiazole by an oxidizing agent to obtain 6-borono-2-(4-nitrophenyl)benzothiazole;
reducing 6-borono-2-(4-nitrophenyl)benzothiazole by a reducing agent to obtain 6-borono-2-(4-aminophenyl)benzothiazole;
reacting 6-borono-2-(4-aminophenyl)benzothiazole, methyl iodide and silver trifluoromethanesulfonate to obtain the compound 6-borono-2-(methyl aminophenyl)benzothiazole of formula I;
wherein the boron in bis(pinacolato)diboron is $^{10}B$.

6. The process according to claim 3, wherein the process for preparing the 6-borono-2-(4-nitrophenyl)benzothiazole comprises steps of:
reacting 6-brom2-(4-nitrophenyl)benzothiazole with bis(pinacolato)diboron to obtain 2-(4-nitrophenyl)-6-(4,4,5,5-tetramethyl-1,3,2-dioxaborolan-2-yl)benzothiazole;
oxidizing 2-(4-nitrophenyl)-6-(4,4,5,5-tetramethyl-1,3,2-dioxaborolan-2-yl)benzothiazole by an oxidizing agent to obtain 6-borono-2-(4-nitrophenyl)benzothiazole.

7. The process according to claim 3, wherein the process for preparing 6-borono-2-(4-aminophenyl)benzothiazole comprises step of:
reducing 6-borono-2-(4-nitrophenyl)benzothiazole to obtain 6-borono-2-(4-aminophenyl)benzothiazole.

8. The process according to claim 5, wherein the carbon in the methyl iodide is $^{11}C$.

9. The process according to claim 4, wherein the oxidizing agent is sodium metaperiodate.

10. The process according to claim 5, wherein the oxidizing agent is sodium metaperiodate.

* * * * *